United States Patent [19]

Thornfeldt

[11] Patent Number: 4,868,219

[45] Date of Patent: Sep. 19, 1989

[54] TREATMENT OF SKIN DISEASES WITH ALIPHATIC AMINES

[76] Inventor: Carl R. Thornfeldt, 1054 NW. 2nd Ave., Ontario, Oreg. 97914

[21] Appl. No.: 178,731

[22] Filed: Apr. 7, 1988

[51] Int. Cl.$^4$ .............................................. A61K 31/13
[52] U.S. Cl. .................................... 514/663; 514/671; 514/859; 514/861; 514/863; 514/864; 514/887
[58] Field of Search ................................ 514/663, 671

[56] References Cited

U.S. PATENT DOCUMENTS

| | | | |
|---|---|---|---|
| 3,485,915 | 12/1969 | Gerstein et al. ................. | 424/65 X |
| 4,067,997 | 1/1978 | Kabara ............................... | 424/312 |
| 4,292,326 | 9/1981 | Nazzaro-Porro .................. | 424/317 |
| 4,386,104 | 5/1983 | Nazzaro-Porro .................. | 424/317 |
| 4,713,394 | 12/1987 | Thornfeldt .......................... | 514/574 |

*Primary Examiner*—Leonard Schenkman
*Attorney, Agent, or Firm*—Townsend and Townsend

[57] ABSTRACT

Noninfectious inflammatory skin diseases in which bacteria or yeasts play a significant adjunctive role are treated with topical formulations of aliphatic amines containing 9 to 18 carbon atoms, and pharmaceutically acceptable salts thereof.

17 Claims, No Drawings

TREATMENT OF SKIN DISEASES WITH ALIPHATIC AMINES

BACKGROUND AND SUMMARY OF THE INVENTION

This invention relates to the treatment of several common skin diseases and premalignant tumors with aliphatic amines having 9 to 18 carbon atoms and pharmaceutically acceptable salts thereof, including hydrohalides. In particular, this invention is a treatment directed against inflammatory and/or hyperproliferative skin diseases in which bacteria or yeasts play a significant adjunctive pathophysiologic role. The present invention resides in the discovery that medium and long chain aliphatic amines and their pharmaceutically acceptable salts effectively treat acne vulgaris, psoriasis, eczema, seborrheic dermatitis, warts, molluscum contagiosum. These compounds may function as primary or adjunctive therapeutic agents.

U.S. Pat. Nos. 4,292,326 (Nazarro-Porro, Sept. 29, 1981) and 4,386,104 (Nazarro-Porro, May 31, 1983) and 4,713,394 (Thornfeldt, Dec. 15, 1987) disclose the use of certain dicarboxylic acids as therapeutic agents for a variety of skin diseases. U.S. Pat. No. 4,067,997 (Kabara, Jan. 10, 1978) discloses the activity against yeast, fungus, and bacteria of a synergistic combination of a 12 carbon atom monocarboxylic acid glycerol ester and a phenolic compound. used as a food preservative.

Acne vulgaris is a multifactorial disease occurring in teenagers and young adults, with inflammatory and noninflammatory comedos on the face and upper trunk. The disease prerequisite is sebaceous glands activated by androgens. For some yet unknown reason hypercornification in the gland duct occurs blocking normal mobility of skin and follicle microorganisms. The restricted environment stimulates release of enzymes (lipases) by Propionobacterium Acnes (an anaerobic corynebacterium). Staphylococcus Epidermidis, and Pitrosporum Ovale (a yeast). Damage to the gland structure and surrounding tissue by the lipases results in inflammatory papules, pustules and cysts, The comedos are free of these microbes. In some, the disease is only manifest as noninflammatory lesions but all patients with inflammatory lesions have some comedos. Major treatments consist of oral and topical antibiotics and retinoids; salicylic acid, sulfu,, and benzoyl peroxide topically, and oral antiandrogen birth control pills.

Psoriasis is a multifactorial disease with epidermal hyperproliferation and epidermal and dermal inflammation producing the lesions. Microbes play an etiologic role since at least 50% of the patients carry Staphylococcus Aureus in the lesions. Beta hemolytic streptococcus is known to cause guttate psoriasis. The psoriasis lesions are sharply demarcated red with thick white scale. They occur predominantly on knees, elbows, scalp, genitalia, and buttocks. Current treatments consist of topical corticosteroids, tar, anthralin, methotrexate azathioprine, etretinate, psoralens plus ultraviolet A light, and tar plus ultraviolet B light.

Eczema is a descriptive term referring to poorly demarcated pruritic, erythematous, scaley, blistered, weeping, fissured or crusted lesions due to many causes. Atopic and numular are the most common types. afflicting any age group. Usually the lesions occur on the face neck, and flexural surfaces. In most patients, there is heavy growth of Staphylococcus Aureus from the lesions of atopic and numular eczema. A purulent rapidly progressive variant, infectious eczematoid, is due to a mixed infection of Staphylococcus Aureus and Streptococcus Pyogenes or either bacteria alone. Current therapy includes topical and systemic corticosteroids. antipruritics, and antibiotics and topical tar.

Warts and molluscum contagiosum are hyperproliferative tumors due to epidermal cell invasion by the Human Papilloma virus and a pox virus, respectively, Unlike other skin virus infections that kill the invaded cells, both these viruses produce hyperplastic, hyperproliferative keratinocytes. Both viruses most commonly infect children. The wart tumors have different morphology depending upon the viral subtype and the thickness of the skin invaded. Molluscum contagiosum are always pearly papules with a central umbilication on an erythematous base. There are currently 23 different chemical and physical destructive treatments, most of which are painful, poorly effective, or may produce systemic toxicity. Poor treatment efficacy in both infections results primarily from the marked tissue hyperplasia induced by the virus. The H.P.V. virus is a proven cancer causing agent.

Seborrheic dermatitis is a histopathologically eczematous dermatosis characterized by poorly demarcated scaley erythematous patches with yellowish greasy scales. "Dandruff" is a mild form of this condition, localized to the scalp. This disease may involve any one, several, or all of the following sites: scalp, eyebrows, glabella, paranasal and chin folds, ears and retroauricular sulci, presternal interscapular regions, pubic regions, and intergluteal folds. Pityrosporum ovale, a yeast, has been shown to play a significant role in 75% of afflicted patients. Present therapy includes corticosteroids, tar, sulfur, and antibiotics, including antiyeast agents.

The conditions described above are the most common skin diseases and tumors, for which it has now been discovered that certain aliphatic amines effectively treat when applied topically. In general, this invention applies to the treatment of inflammatory and hyperproliferative skin diseases in which bacteria play a significant supporting pathophysiologic role.

DETAILED DESCRIPTION OF THE INVENTION AND PREFERRED EMBODIMENTS

The aliphatic amines of the present invention are those having 9 to 18 carbon atoms, inclusive, with 12 to 16 carbon atoms preferred. The compounds include straight-chain and branched-chain species, and saturated and unsaturated species, including species with multiple unsaturation sites. Preferred among these are straight-chain species, either saturated or unsaturated. Examples include dodecylamine, tetradecylamine myristoleylamine (cis-tetradec-9-enylamine), hexadecylamine palmitoleylamine (cis-hexadec-9-enylamine), octadecylamine, linoleylamine (octadeca-9,12-dienylamine), and linolenylamine (octadeca-9,12,15-trienylamine). Preferred salts of the amines of the present invention are hydrohalide, particularly hydrochloride salts. A prime example is dodecylamine hydrochloride, particularly laurylamine (n-dodecylamine) hydrochloride.

The compounds are generally applied in dermatological formulations. These include any of the various known mixtures and combinations which may be applied topically and will permit even spreading of the active ingredient over the affected area.

Examples include creams, lotions, solutions, ointments, and unguents.

The concentration of the aliphatic amine in the formulation is not critical and may vary over a wide range. The concentration may indeed range as high as the upper limit of dissolvability in any given formulation. In most cases, however, best results are achieved within a range of about 0.1% to about 35% by weight, preferably from about 1% to about 10% by weight.

The formulation may contain additional ingredients on an optional basis, including both those which are biologically active and those which are biologically inactive. Keratolytic agents are particularly useful in some cases as added active ingredients. Examples are salicylic acid, sulfur and retinoid derivatives. Optional concentrations will vary among keratolytic agents. Salicylic acid, for example, is preferably used at about 0.5% to about 5.0% while sulfur is preferably used at about 2.0% to about 10.0%. Appropriate concentration ranges for any particular keratolytic agent will be apparent to those skilled in the art.

Stratum corneum penetration enhancing compounds are usually included in dermatologic formulations to boost efficacy. Examples include propylene glycol, sodium lauryl sulfate, dimethylamide N-methyl-2-pyrrolidone, and Azone (Nelson Research, Irvine, Calif.).

Examples of inactive ingredients are wetting agents, surfactants, emollients, and solvents.

The term "therapeutically effective amount" is used herein to denote any amount which will cause a substantial improvement in a disease condition (such as a subsidence of a lesion, for example) when applied to the affected area repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The term "pharmaceutically acceptable salts" is used herein to denote salts of the amines which are biologically compatible and otherwise suitable for administration to human subjects, and which deliver the therapeutic activity of the amine to the subject in substantially the same degree as if the amine itself were administered.

The compositions are generally applied in topical manner to the affected area, i.e., localized application to the skin region where the inflammation or hyperproliferation abnormality or tumor is manifest.

The foregoing description is offered primarily for purposes of illustration. It will be readily apparent to those skilled in the art and numerous variations in both the formulations and their method of use, not mentioned above, may be made without departing from the spirit and scope of the invention.

What is claimed is:

1. A method for the treatment of skin suffering from noninfectious inflammatory diseases in which bacteria or yeasts play an adjunctive role, said method comprising applying to the affected area a therapeutically effective amount of a dermatological formulation containing from about 0.1% to about 35% by weight of a compound selected from the group consisting of aliphatic amines having 9 to 18 carbon atoms, and pharmaceutically acceptable salts thereof.

2. A method for the treatment of skin suffering from psoriasis, acne vulgaris, seborrheic dermatitis, atopic eczema, or numular eczema, said method comprising applying to the affected area a therapeutically effective amount of a dermatological formulation containing from about 0.1% to about 35% by weight of a compound selected from the group consisting of aliphatic amines having 9 to 18 carbon atoms, and pharmaceutically acceptable salts thereof.

3. A method in accordance with claim 2 in which said dermatological formulation contains from about 1% to about 10% by weight of said compound, and said aliphatic amines have 12 to 16 carbon atoms.

4. A method in accordance with claim 2 in which sid dermatological formulation contains from about 1% to about 10% by weight of said compound, and said compound is a dodecylamine hydrochloride.

5. A method in accordance with claim 2 in which said dermatological formulation contains from about 1% to about 10% by weight of said compound, and said compound is laurylamine hydrochloride.

6. A method in accordance with claim 2 in which said dermatological formulation contains from about 1% to about 10% by weight of said compound, and said compound is myristoleylamine hydrochloride.

7. A method in accordance with claim 2 in which said dermatological formulation contains from about 1% to about 10% by weight of said compound, and said compound is palmitoleylamine hydrochloride.

8. A method in accordance with claim 2 in which said dermatological formulation contains from about 1% to about 10% by weight of said compound, and said compound is linoleylamine hydrochloride.

9. A method in accordance with claim 2 in which said dermatological formulation contains from about 1% to about 10% by weight of said compound, and said compound is linolenylamine hydrochloride.

10. A method for the treatment of skin suffering from warts or molluscum contagiosum, said method comprising applying to the affected area a therapeutically effective amount of a dermatological formulation containing from about 0.1% to about 35% by weight of a compound selected from the group consisting of aliphatic amines having 9 to 18 carbon atoms, and pharmaceutically acceptable salts thereof.

11. A method in accordance with claim 10 in which said dermatological formulation contains from about 1% to about 10% by weight of said compound, and said aliphatic amines have 12 to 16 carbon atoms.

12. A method in accordance with claim 10 in which said dermatological formulation contains from about 1% to about 10% by weight of said compound, and said compound is a dodecylamine hydrochloride.

13. A method in accordance with claim 10 in which said dermatological formulation contains from about 1% to about 10% by weight of said compound, and said compound is laurylamine hydrochloride.

14. A method in accordance with claim 10 in which said dermatological formulation contains from about 1% to about 10% by weight of said compound, and said compound is myristoleylamine hydrochloride.

15. A method in accordance with claim 10 in which said dermatological formulation contains from about 1% to about 10% by weight of said compound, and said compound is palmitoleylamine hydrochloride.

16. A method in accordance with claim 10 in which said dermatological formulation contains from about 1% to about 10% by weight of said compound, and said compound is linoleylamine hydrochloride.

17. A method in accordance with claim 10 in which said dermatological formulation contains from about 1% to about 10% by weight of said compound, and said compound is linolenylamine hydrochloride.

* * * * *